US012805530B2

(12) United States Patent
Shimizu et al.

(10) Patent No.: US 12,805,530 B2
(45) Date of Patent: Nov. 24, 2026

(54) *LYSINIBACILLUS* BACTERIAL STRAIN THAT PROMOTES PLANT GROWTH, AND USE THEREOF

(71) Applicants: NATIONAL UNIVERSITY CORPORATION TOKAI NATIONAL HIGHER EDUCATION AND RESEARCH SYSTEM, Nagoya (JP); Kumiai Chemical Industry Co., Ltd., Taito-ku (JP)

(72) Inventors: Masafumi Shimizu, Nagoya (JP); Katsumi Furuse, Taito-ku (JP)

(73) Assignees: NATIONAL UNIVERSITY CORPORATION TOKAI NATIONAL HIGHER EDUCATION AND RESEARCH SYSTEM, Nagoya (JP); Kumiai Chemical Industry Co., Ltd., Taito-ku (JP)

( * ) Notice: Subject to any disclaimer, the term of this patent is extended or adjusted under 35 U.S.C. 154(b) by 214 days.

(21) Appl. No.: 18/555,813

(22) PCT Filed: May 27, 2022

(86) PCT No.: PCT/JP2022/021838

§ 371 (c)(1),
(2) Date: Oct. 17, 2023

(87) PCT Pub. No.: WO2022/255274

PCT Pub. Date: Dec. 8, 2022

(65) Prior Publication Data

US 2024/0196907 A1 Jun. 20, 2024

(30) Foreign Application Priority Data

May 31, 2021 (JP) ................................ 2021-091892

(51) Int. Cl.
*A01N 63/22* (2020.01)
*A01C 1/06* (2006.01)
*A01P 21/00* (2006.01)
*C12N 1/20* (2026.01)

(52) U.S. Cl.
CPC ................ *A01N 63/22* (2020.01); *A01C 1/06* (2013.01); *A01P 21/00* (2021.08); *C12N 1/20* (2013.01)

(58) Field of Classification Search
CPC ......... A01N 63/22; A01N 63/20; A01P 21/00; C12N 1/20; C12R 2001/01
See application file for complete search history.

(56) References Cited

FOREIGN PATENT DOCUMENTS

| | | |
|---|---|---|
| CN | 108676745 | * 10/2018 |
| CN | 108676745 A | * 10/2018 |

OTHER PUBLICATIONS

Lee et al (*Lysinibacilus xylanilyticus* sp. nov. a xylan-degrading bacterium isolated from forest humus), International Journal of Systemiatic and Evolutionary Microbiology (2010), 60, 281-286.*

Naureen et al (Exploring the Potentials of Lysinibacillus sphaericus ZA9 for Plant Growth Promotion and Biocontrol Activities against Phytopathogenic Fungi), Frontiers in Microbiology, Original Research, Aug. 2017.*

International Search Report mailed on Aug. 9, 2022 in PCT/JP2022/021838 filed on May 27, 2022 (2 pages).

Dhondge. H. V. et al. "Rhizobacterial consortium mediated aroma and yield enhancement in basmati and non-basmati rice (*Oryza sativa* L.)", J. Biotechnol. 2021. vol. 328. pp. 47-58. Available online: Jan. 18, 2021.

Passera. A. et al. "Characterization of Lysinibacillus fusiformis strain S4C11: In vitro. in planta, and in silico analyses reveal a plant-beneficial microbe", Microbial. Res., 2021. vol. 244,126665, 17 pages, Available online: Dec. 5, 2020.

Sahu. P. K. et al. "Effect of bacterial endophytes *Lysinibacillus* sp. on plant growth and fruit yield of tomato (*Solanum lycopersicum*)", Int. J. Curr. Microbial. App. Sci., 2018. vol. 7. No. 5. pp. 3399-3408.

Sharma. N. et al. "Role of Lysinibacillus sphaericus SNCh5 bacterial strain as bio-inoculant for agriculture practice", Int. J. Curr., Microbial. App. Sci., 2015. vol. 4. No. 12. pp. 484-500.

Ahsan. N. et al. "Lysinibacillus xylanilyticus strain GIC41 as a potential plant biostimulant", Microbes Environ., 2021. vol. 36. No. 4. ME21047, 10 pages.

* cited by examiner

*Primary Examiner* — Mina Haghighatian
(74) *Attorney, Agent, or Firm* — Oblon, McClelland, Maier & Neustadt, L.L.P.

(57) ABSTRACT

A naturally derived, safe-to-use microbial material that can contribute to increasing agricultural production by promoting crop growth and increasing yield, while controlling plant disease at the same time. Viable bacteria of a novel bacterial strain of genus *Lysinibacillus*, or a culture containing the viable bacteria, are used as an active component. The novel bacterial strain may be *Lysinibacilus xylanilyticus* GIC41 (NITE BP-03464). A plant growth regulator contains the bacterial strain and promotes crop growth and increases yield. A plant disease control agent that contains the bacterial strain is capable of controlling a disease, such as by damping-off.

11 Claims, 2 Drawing Sheets

*LYSINIBACILLUS* BACTERIAL STRAIN THAT PROMOTES PLANT GROWTH, AND USE THEREOF

CROSS REFERENCE TO RELATED APPLICATIONS

This application is a National Stage entry under 35 U.S.C. § 371 of PCT/JP2022/021838 filed on May 27, 2022, and claims priority to Japanese Patent Application No. 2021-091892, filed on May 31, 2021, the entire contents of which are incorporated herein by reference.

BACKGROUND OF THE INVENTION

1. Field of the Invention

The present invention relates to a bacterial strain of genus *Lysinibacillus* having a plant growth promoting effect, and use thereof.

2. Description of Related Art

Promotion of crop growth for increased yield has been more important than ever amid projections of increasing world populations, worldwide desertification, and climate change due to global warming in a world with limited arable areas. The breeding, fertilization, and cultivation techniques have evolved over the years to achieve high yields. However, there is a growing need for newer and more versatile tools. In the field of agrichemicals, there has been development of plant growth regulators; however, greater concern over environmental issues in the last years has created a large demand for naturally derived materials.

Among such natural materials are Mamerich® for soybeans, and Yume-Bio® for paddy rice cultivation, which were recently developed as materials using microorganisms. However, these are applicable to only limited types of crops.

Against such a technical backdrop, there is a demand for development of a more versatile, naturally derived material capable of promoting crop growth to increase yield.

Damage to agricultural crops from disease also remains a challenging issue, and a wide range of approaches are taken against this problem, including cultural or physical control using rotational cropping or solar heat, chemical control using chemical pesticides, and control using disease-resistant varieties. However, it cannot be said that these are satisfactory. Control by chemical pesticides has become a serious global issue because of the emergence of drug-resistant bacteria potentially undermining the effect of chemical pesticides. The occurrence of soil-borne diseases that are difficult to control with chemical pesticides is also a serious problem in many parts of the world.

As discussed above, there is a need for the development of a novel control technique using a naturally occurring microorganism also in disease control of agricultural crops.

CITATION LIST

Non Patent Literature

NPL 1: Green Report No. 621 p. 21

NPL 2: Journal of Japanese Society of Soil Science and Plant Nutrition, Vol. 92, No. 1, pp. 36 to 41

SUMMARY OF THE INVENTION

The present invention was made with an objective to provide a naturally derived, safe-to-use microbial material that can contribute to increasing agricultural production by promoting crop growth and increasing yield while controlling plant disease at the same time.

The present inventors conducted diverse studies to achieve the foregoing object, and found that a novel bacterial strain of genus *Lysinibacillus*, unknown in the past, separated from paddy soil in Mie prefecture, Japan, has the effect to promote crop growth and increase yield while controlling plant disease at the same time. The present invention was completed on the basis of this finding.

Specifically, embodiments of the present invention are as follows.

(1) A novel *Lysinibacillus xylanilyticus* GIC41 bacterial strain (NITE BP-03464).

(2) The bacterial strain according to (1), which has a plant growth regulatory effect.

(3) The bacterial strain according to (2), wherein the plant growth regulatory effect is a plant growth promoting effect or a plant growth inhibitory effect.

(4) The bacterial strain according to any one of (1) to (3), which increases plant yield with a plant growth promoting effect.

(5) The bacterial strain according to (1), which has a plant disease control effect.

(6) The bacterial strain according to any one of (1) to (5), which has both a plant growth regulatory effect and a plant disease control effect.

(7) A plant growth regulator comprising the bacterial strain of any one of (1) to (4), and (6), and/or a culture of the bacterial strain as an active component.

(8) The plant growth regulator according to (7), which is a growth regulator for Amaranthaceae plants (including Chenopodiaceae plants) and Solanaceae plants.

(9) A plant disease control agent comprising the bacterial strain of any one of (1), (5), and (6), and/or a culture of the bacterial strain as an active component.

(10) The plant disease control agent according to (9), which is a soil-borne disease control agent.

(11) The plant disease control agent according to (9) or (10), which is a damping-off control agent for crops.

(12) The plant disease control agent according to any one of (9) to (11), which is a plant disease control agent for Amaranthaceae plants (including Chenopodiaceae plants).

(13) The plant growth regulator and the plant disease control agent according to any one of (7) to (12), which have both a plant growth regulatory effect and a plant disease control effect.

(14) A method for regulating plant growth and/or preventing plant disease, comprising the step of contacting viable bacteria of one or more of the bacterial strains of (1) to (6), or a culture containing the viable bacteria, to a plant and/or soil (particularly, the rhizosphere).

(15) The method according to (14), wherein the plant is a plant seed.

(16) The method according to (14) or (15), wherein the viable bacteria or a culture containing the viable bacteria are contacted to soil by irrigation or mixing into the soil.

Other embodiments of the present invention are as follows.

(17) A novel *Lysinibacillus xylanilyticus* GIC41 bacterial strain (NITE BP-03464).

(18) The bacterial strain according to (17), which increases yield by promoting plant growth.

(19) The bacterial strain according to (18), which additionally has a plant disease control effect.

(20) A plant growth regulator comprising the bacterial strain of (17) or a culture of the bacterial strain as an active component.

(21) The plant growth regulator according to (20), which is a plant growth regulator for Amaranthaceae plants and Solanaceae plants.

(22) A plant disease control agent comprising the bacterial strain of (17) or a culture of the bacterial strain as an active component.

(23) The plant disease control agent according to (22), which is a control agent against soil-borne plant disease.

(24) The plant disease control agent according to (23), which is a damping-off control agent for crops.

(25) The plant disease control agent according to any one of (22) to (24), which is a control agent for Amaranthaceae plants.

(26) A method for promoting plant growth and/or preventing plant disease, comprising the step of contacting viable bacteria of one or more of the bacterial strains of (17) to (19), or a culture containing the viable bacteria, to a plant and/or soil (particularly, the rhizosphere).

(27) The method according to (26), wherein the plant is a plant seed.

(28) The method according to (26), wherein the viable bacteria or a culture containing the viable bacteria are contacted to soil by irrigation or mixing into the soil.

Advantageous Effects of Invention

The present invention enables control of, for example, a soil-borne plant disease, which has been difficult to control in the past, while promoting crop growth and increasing yield, simply with the use of a single naturally occurring bacterial strain. Specifically, the present invention can provide a material that can contribute to crop production by increasing profit with its plant growth regulatory effect while reducing loss by controlling disease.

DESCRIPTION OF THE PREFERRED EMBODIMENTS

Figure 1:
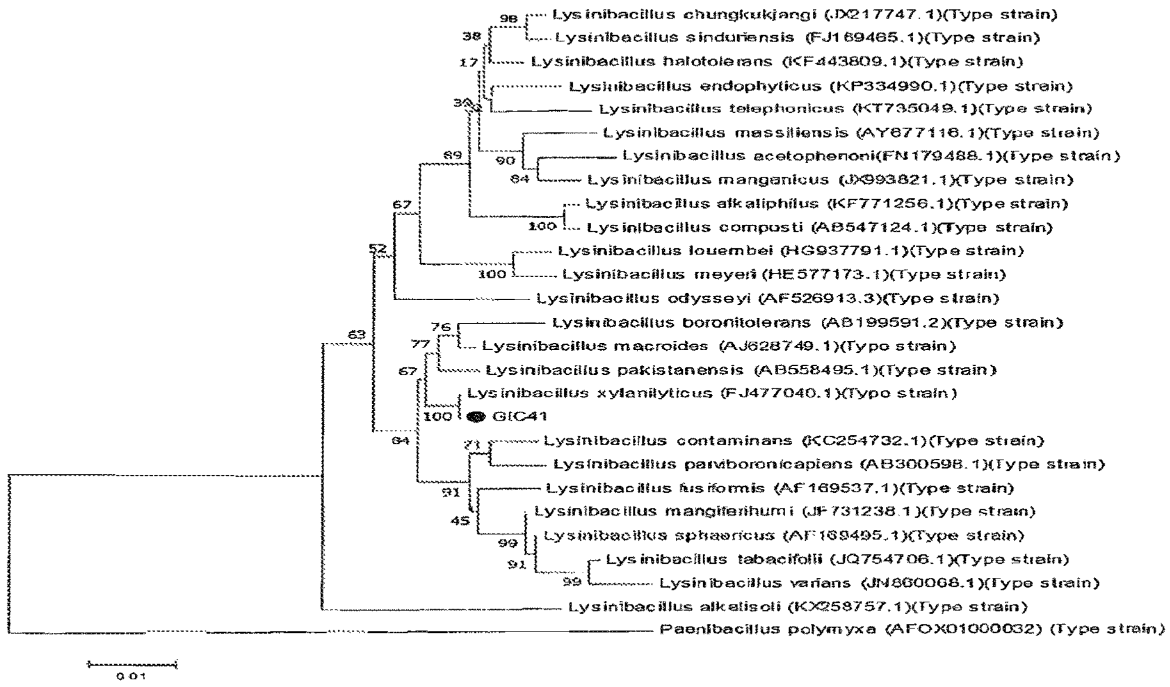
FIG. 1 shows where the GIC41 bacterial strain is located in a molecular phylogenetic tree based on the base sequence of the 16S-rRNA gene.

In order to achieve the foregoing object, the present inventors searched a wide range of microorganisms. The search found, for the first time, that the bacterial strain successfully separated by the present inventors is a novel bacterial strain that was not known in the past, and that the novel bacterial strain alone has the new and useful effect of promoting plant growth and controlling plant disease.

Specifically, the present invention separated a novel bacterial strain, and found, for the first time, that the novel bacterial strain has the new effect of promoting plant growth and controlling damping-off. These findings were systematically combined, and the present invention was completed after further studies.

The present invention uses a bacterial strain of genus *Lysinibacillus* as an active component of, for example, a plant growth regulator and a soil-borne plant disease control agent. In the present invention, plant growth regulation includes promotion and inhibition of plant growth, and "promotion of plant growth" means to significantly increase the size, weight, and other traits of a plant by treatment with a bacterial strain of the present invention, relative to plants not affected by any factors that inhibit plant growth, for example, such as disease or insect damage.

Preferably, the strain used in the present invention is the GIC41 bacterial strain, or a GIC41 mutant strain retaining properties similar to the properties of the GIC41 bacterial strain, isolated from paddy soil in Mie prefecture, Japan, and identified as a novel bacterial strain of the non plant-pathogenic species *Lysinibacillus xylanilyticus* after studies of bacteriologic properties and phylogenetic analysis of the genome sequence of the 16S rRNA gene. The GIC41 bacterial strain has been shown to have the following bacteriologic properties by tests conducted using an API20NE Kit (available from Sysmex bioMerieux Co., Ltd.).

GIC41 Bacterial Strain

The GIC41 bacterial strain has the following bacteriologic properties.

(A) Morphological properties
- Morphology: Rod-shaped
- Size: 0.9 to 1.5 m×3.3 to 6.0 m
- Mobility: Present (B) Culture properties
- Color of colony: Pale beige to beige Colony morphology:
- Shape: Circular
- Elevation: Flat to convex
- Margin: Entire (C) Physiological properties
- Gram staining: Positive
- Growth pH: Neutral range of 5.5 to 8.0 (optimum pH: 6.5 to 8.0)
- Growth temperature: 20 to 40° C. (optimum temperature: 30° C.)
- Nitrate reduction: +
- Indole production (triptophan): +
- Glucose fermentation: −
- Arginine dihydrolase: −
- Urease: +
- Hydrolysis (β-glucosidase): +
- Hydrolysis (protease): +
- Hydrolysis (β-galactosidase): −
- Assimilation (glucose): +
- Assimilation (arabinose): +
- Assimilation (mannose): +
- Assimilation (mannitol): +
- Assimilation (N-acetyl-glucosamine): +
- Assimilation (maltose): +
- Assimilation (potassium gluconate): +
- Assimilation (capric acid): −
- Assimilation (adipic acid): +
- Assimilation (maleate): +
- Assimilation (trisodium citrate): +
- Assimilation (phenyl acetate): +

A unique feature of the present bacterial strain is that the bacterial strain has both the effect to regulate plant growth and the effect to control plant disease.

The GIC41 bacterial strain has been internationally deposited at The National Institute of Technology and Evaluation, NITE Patent Organism Depositary (2-5-8, Kazusa-Kamatari, Kisarazu-shi, Chiba, 292-0818, Japan; Apr. 21, 2021) with the deposition number NITE BP-03464.

The present bacterial strain *Lysinibacillus xylanilyticus* GIC41 is indicated as *Lysinibacillus* sp. GIC41 in the certificate.

Any medium can be used for culture of the GIC41 bacterial strain of the present invention, provided that it allows bacterial strains of genus *Lysinibacillus* to grow. Examples include common media such as bouillon medium, and media containing glucose, peptone, and yeast extract. The medium may be a liquid medium, or a solid medium such as an agar-supplemented slant or plate medium.

As a carbon source of the medium, any source can be utilized that can be assimilated by strains belonging to genus *Lysinibacillus*. Specific examples include various synthetic and natural carbon sources that can be utilized by strains of genus *Lysinibacillus*, such as glucose, arabinose, mannose, starch hydrolysate, and molasses. The nitrogen source in medium may be chosen from a variety of synthetic and natural products that can be utilized by the strains, including, for example, organic nitrogen-containing products such as peptone, meat extract, yeast extract, and soybean meal. Additionally, trace amounts of nutrient sources may be added according to the customary method of microbial culture, as required. Examples of such nutrient sources include inorganic salts such as common salt and phosphates; metal salts such as calcium, magnesium, and iron salts; vitamins, amino acids, and nucleic acid-related substances. It is also possible to add an additive, for example, such as a defoaming agent, as required.

The GIC41 bacterial strain of the present invention may be cultured under aerobic conditions, for example, such as shaking culture or aeration culture, as with other bacterial strains of genus *Lysinibacillus*. The culture conditions are not limited to these, and the strain may be cultured for 0.5 to 3 days, preferably 1 to 2 days at a temperature of 20 to 40° C., preferably 25 to 30° C., at pH 5.5 to 8, preferably 6.5 to 8.

After being cultured in the manner described above, the GIC41 bacterial strain of the present invention can be used as an active component of, for example, a plant growth regulator or a plant disease control agent, in the form of a culture containing viable bacteria of this strain, without separating the strain from the culture. Alternatively, the viable bacteria may be separated from the culture using an ordinary method, for example, such as by membrane separation or centrifugation, and the separated bacteria, after optional washing, may be used as an active component as it is or after treatment (for example, as a mixture with other components). It is also possible to use the bacterial culture or separated viable bacteria in the form of a dried product obtained by using a technique such as freeze drying or spray drying, or in the form of a diluted product obtained by diluting a liquid or solid of the cultured bacteria or separated bacteria. The cultured bacteria or separated bacteria also may be used in the form of various preparations produced by mixing various additives using the traditional methods of producing pesticide formulations. Examples of such preparations include granular formulations, emulsions, wettable powders, and flowable formulations.

The concentration of viable bacteria contained in the agents of the present invention, including a plant growth regulator and a soil-borne plant disease control agent, is not particularly limited, as long as the agents can produce the desired effect. However, because a bacterial concentration that is too low often fails to produce sufficient results, and a bacterial concentration that is too high is usually wasteful of bacteria, the bacterial concentration may be appropriately adjusted in a range of $1\times10^5$ to $1\times10^{11}$ cfu/ml, preferably $1\times10^6$ to $1\times10^{10}$ cfu/ml, in the case of, for example, a liquid preparation. As used herein, “cfu” means colony forming unit. When using a culture, the culture may be appropriately designed according to these ranges of viable bacteria concentration. Instead of cfu, the bacterial concentration may be represented by absorbance at 600 nm ($OD_{600}$). For example, an $OD_{600}$ value of 0.5 roughly corresponds to $1.0\times10^7$ ? cfu/ml under 30° C., 200 rpm, 48-hour shake culture conditions using NB medium. However, the value depends on the state of the strain and culture conditions, and the measured value does not necessarily correspond to this value.

Examples of plants for which the growth promotion and disease control by the GIC41 bacterial strain of the present invention can be expected include cereals (for example, rice, wheat, barley, corn, and buckwheat), potatoes (for example, potato, sweet potato, taro, and yam), peas (for example, soybean, common bean, azuki bean, and pea), vegetables (for example, melon, tomato, eggplant, green pepper, cabbage, napa cabbage, daikon, lettuce, carrot, long green onion, bulb onion, strawberry, spinach, sugar beet, beet, chard, and celery), fruits (for example, apple, pear, cherry, peach, grape, oriental persimmon, citrus fruits, and kiwi), industrial crops (for example, cotton, rapeseed, common sunflower, beet, sugar cane, and tobacco), lawn grass, trees, and ornamental plants (for example, rose, mum, tulip, baby’s breath, and lisianthus). However, the present invention is not limited to these examples.

Specific examples of plant pathogens that can be controlled with the GIC41 bacterial strain of the present invention include *Pseudoperonospora* (e.g., *Pseudoperonospora cubensis*), *Venturia* (e.g., *Venturia inaequalis*), *Erysiphe* (e.g., *Erysiphe graminis*), Pyricularia (e.g., Pyricularia *oryzae*), *Botrytis* (e.g., *Botrytis cinerea*), *Rhizoctonia* (e.g., *Rhizoctonia solani*), *Cladosporium* (e.g., *Cladosporium fulvum*), *Colletotrichum* (e.g., *Colletotrichum fragariae*), *Puccinia* (e.g., *Puccinia recondita*), *Septoria* (e.g., *Septoria nodorum*), *Sclerotinia* (e.g., *Sclerotinia sclerotiorum*), *Pythium* (e.g., *Pythium debaryanum* Hesse), and Gaeumannomyces (e.g., Gaeumannomyces *graminis*. Examples of bacteria include *Pseudomonas syringae*. However, the present invention is not limited to these examples.

A plant growth regulator and/or a plant disease control agent according to the present invention may be applied as it is, or after being diluted with, for example, water. Use as a pesticidal formulation is not particularly limited, and, for example, the plant growth regulator or plant disease control agent may be directly applied to crops or seeds by being sprayed to crops or seeds, or crops or seeds may be dipped in the plant growth regulator or plant disease control agent. As another example, the plant growth regulator or plant disease control agent may be sprayed onto soil, or may be applied by irrigating soil or by being added to water or fertilizers added to crops and soil. As yet another example, the plant growth regulator or plant disease control agent may be applied to farm equipment. Preferably, the plant growth regulator or plant disease control agent is directly sprayed to crops. That is, a plant growth regulator and/or a plant disease control agent according to the present invention promote plant growth and increase yield, and inhibit plant disease by being present on a plant, for example, on the root, stems, leaves, or seeds of a plant, or in the soil used for cultivation.

A pesticidal formulation of the present invention is used in amounts that depend on factors such as the type of the crop of interest, the type of the disease to be controlled, the method of application, patterns of disease occurrence, extent of damage, environmental conditions, and the form of formulation. Accordingly, no specific amounts are set, and the pesticidal formulation is preferably used in appropriately adjusted amounts. As an example, in the case of a liquid formulation, the pesticidal formulation is used in an amount of 30 ml to 1 L, preferably 50 ml to 1 L per stock of a crop plant. The time to use the pesticidal formulation also depends on factors such as the type of the disease to be controlled, and the form of pesticidal formulation. Preferably, the pesticidal formulation is applied at an appropriate time within 2 weeks before or after planting. In the present invention, there is no concern about the emergence of resistant plant pathogens, and the microbial pesticide of the present invention can be continuously used for several days, or can be used also for continuous cropping.

A soil-borne plant disease control agent according to the present invention may be used with other fertilizers and agrichemicals, for example, such as germicides, antiviral agents, insecticides, miticides, nematicides, synergists, attractants, herbicides, and plant growth regulators, as required. In this case, these may be applied after being prepared into a mixture under conditions that have only little effect on the active component strain, or may be applied, separately from the soil-borne plant disease control agent at a different time or simultaneously with the soil-borne plant disease control agent.

The following compounds are non-limiting examples of known germicides (germicidal active components) and disease control agents that can be used as a mixture or in combination.

Germicidal Active Components or Disease Control Agents *Agrobacterium radiobacter*, azaconazole, acibenzolar-S-methyl, azoxystrobin, anilazine, amisulbrom, aminopyrifen, ametoctradin, aldimorph, isotianil, isopyrazam, isofetamid, isoflucypram, isoprothiolane, ipconazole, ipflufenoquin, ipfentrifluconazole, iprodione, iprovalicarb, iprobenfos, imazalil, iminoctadine-albesilate, iminoctadine-triacetate, imibenconazole, inpyrfluxam, imprimatin A, imprimatin B, edifenphos, etaconazole, ethaboxam, ethirimol, ethoxyquin, etridiazole, enestroburin, enoxastrobin, epoxiconazole, organic oils, oxadixyl, oxazinylazole, oxathiapiprolin, oxycarboxin, oxine-copper, oxytetracycline, oxpoconazole-fumarate, oxolinic acid, copper dioctanoate, octhilinone, ofurace, orysastrobin, o-phenylphenol, kasugamycin, captafol, carpropamid, carbendazim, carboxin, carvone, *Candida oleophila, Candida saitoana*, quinoxyfen, quinofumelin, chinomethionat, captan, quinconazole, quintozene, guazatine, cufraneb, coumethoxystrobin, coumoxystrobin, *Gliocradium catenulatum, Cryptococcus albidus*, kresoxim-methyl, clozylacon, *Clonostachys rosea*, chlozolinate, chloroinconazide, chlorothalonil, chloroneb, *Chaetomium cupreum, Coniothyrium minitans*, cyazofamid, diethofencarb, diclocymet, dichlofluanid, dichlobentiazox, diclomezine, dicloran, dichlorophen, dithianon, diniconazole, diniconazole-M, zineb, dinocap, dipymetitrone, diphenylamine, difenoconazole, cyflufenamid, diflumetorim, cyproconazole, cyprodinil, simeconazole, dimethirimol, dimethyl disulfide, dimethomorph, cymoxanil, dimoxystrobin, *Pseudozyma flocculosa, Pseudomonas aureofaciens, Pseudomonas chlororaphis, Pseudomonas syringae, Pseudomonas flurorescens, Pseudomonas rhodesiae*, ziram, silthiofam, Zucchini yellow mosaic virus-WK, streptomycin, *Streptomyces griseoviridis, Streptomyces* lygicus, spiroxamine, sedaxane, seboctylamine, zoxamide, solatenol, dazomet, *Talaromyces flavus*, tiadinil, thiabendazole, thiram, thiophanate, thiophanate-methyl, thifluzamide, thiram, tecnazene, tecloftalam, tetraconazole, debacarb, tebuconazole, tebufloquin, terbinafine, dodine, dodemorph, triadimenol, triadimefon, triazoxide, trichlamide, triclopyricarb, *Trichoderma asperellum, Trichoderma* atroviride, *Trichoderma gamsii, Trichoderma stromaticum, Trichoderma harzianum, Trichoderma viride, Trichoderma virens, Trichoderma polysporum, Trichoderma lignorum*, tricyclazole, triticonazole, tridemorph, triflumizole, trifloxystrobin, triforine, tolylfluanid, tolclofos-methyl, tolnifanide, tolprocarb, nabam, natamycin, naftifine, nitrapyrin, nitrothal-isopropyl, nuarimol, copper nonyl phenol sulphonate, *Paenibacillus polymyxa, Barkholderia cepacia, Bacillus amyloliquefaciens, Bacillus simplex, Bacillus subtilis, Bacillus pumilus, Bacillus licheniformis*, harpin protein, *Variovorax paradoxus*, validamycin, valifenalate, *Pantoea agglomerans*, picarbutrazox, bixafen, picoxystrobin, *Pythium oligandrum*, pydiflumetofen, bitertanol, binapacryl, hinokitiol, non-pathogenic *Erwinia carotovora*, non-pathogenic *Rhizobium vitis*, biphenyl, piperalin, hymexazol, pyraoxystrobin, pyraclostrobin, pyraziflumid, pyrazophos, pyrapropoyne, pyrametostrobin, pyriofenone, pyrisoxazole, pyridachlometyl, pyrifenox, pyributicarb, pyribencarb, pyrimethanil, pyroquilon, vinclozolin, ferbam, famoxadone, phenazine oxide, fenamidone, fenaminstrobin, fenarimol, fenoxanil, ferimzone, fenpiclonil, fenpicoxamid, fenpyrazamine, fenbuconazole, fenfuram, fenpropidin, fenpropimorph, fenhexamid, folpet, phthalide, *Fusarium oxysporum*, bupirimate, fuberidazole, blasticidin-S, furametpyr, furalaxyl, furancarboxylic acid, fluazinam, fluindapyr, fluoxastrobin, fluoxapiprolin, fluoxytioconazole, fluopicolide, fluopimomide, fluopyram, fluoroimide, fluxapyroxad, fluquinconazole, furconazole, furconazole-cis, fludioxonil, flusilazole, flusulfamide, flutianil, flutolanil, flutriafol, flufenoxadiazam, flufenoxystrobin, flubeneteram, flumetylsulforim, flumetover, flumorph, *Phlebiopsis gigantea*, proquinazid, prochloraz, procymidone, prothiocarb, prothioconazole, bronopol, propamocarb-hydrochloride, propiconazole, propineb, probenazole, bromuconazole, flometoquin, florylpicoxamid, hexaconazole, benalaxyl, benalaxyl-M, benodanil, benomyl, pefurazoate, penconazole, pencycuron, benzovindiflupyr, benthiazole, benthiavalicarb-isopropyl, penthiopyrad, penflufen, boscalid, fosetyl (including salts, for example, such as aluminum, calcium, and sodium salts), polyoxin, polycarbamate, Bordeaux mixture, mancopper, mancozeb, mandipropamid, mandestrobin, maneb, myclobutanil, Mitsuaria chitosanitabida, mineral oils, mildiomycin, methasulfocarb, metam, metalaxyl, metalaxyl-M, metarylpicoxamid, metiram, metyltetraprole, metconazole, metominostrobin, metrafenone, mepanipyrim, mefentrifluconazole, meptyldinocap, mepronil, iodocarb, laminarin, phosphorous acid and salts, copper oxychloride, silver, copper(II) acetate, cuprous oxide, copper hydroxide, potassium bicarbonate, sodium bicarbonate, sulfur, oxyquinoline sulfate, copper sulfate, 3,4-dichloroisothiazol-5-yl)methyl 4-(tert-butyl)benzoate (IUPAC name; CAS Registry Number: 1231214-23-5), UK-2A (Code Number), dodecylbenzenesulfonic acid bisethylenediamine copper [II] salt (DBEDC), triphenyltin acetate (TPTA), triphenyltin chloride (TPTC), and triphenyltin hydroxide (TPTH).

The following are non-limiting examples of known insecticides (insecticidal active components), miticides (miticidal active components), nematicides (nematicidal active components), and synergist compounds (synergistical active components) that can be used as a mixture or in combination.

Insecticidal Active Components, Miticidal Active Components, Nematicidal Active Components, and Synergistical Active Components Acrinathrin, azadirachtin, azamethiphos, acynonapyr, azinphos-ethyl, azinphos-methyl, acequinocyl, acetamiprid, acetoprole, acephate, azocyclotin, abamectin, afidopyropen, afoxolaner, amidoflumet, amitraz, alanycarb, aldicarb, aldoxycarb, allethrin [including d-cis-trans-form and d-trans-form], isazophos, isamidofos, isocarbophos, isoxathion, isocycloseram, isofenphos-methyl, isoprocarb, epsilon-metofluthrin, epsilon-momfluorothrin, ivermectin, imicyafos, imidacloprid, imiprothrin, indoxacarb, esfenvalerate, ethiofencarb, ethion, ethiprole, ethylene dibromide, etoxazole, etofenprox, ethoprophos, etrimfos, emamectin, emamectin benzoate, endosulfan, empenthrin, oxazosulfyl, oxamyl, oxydemeton-methyl, oxydeprofos, omethoate, nuclear polyhedrosis virus, cadusafos, kappa-tefluthrin, kappa-bifenthrin, karanjin, cartap, granulosis virus, carbaryl, carbosulfan, carbofuran, gamma-BHC, xylylcarb, quinalphos, kinoprene, chinomethionat, enterovirus, coumaphos, cryolite, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, chloroprallethrin, entomopoxivirus, iridovirus, cyazypyr, cyanophos, diafenthiuron, diamidafos, cyantraniliprole, cyetpyrafen, dienochlor, cyenopyrafen, dioxabenzofos, diofenolan, sigmavirus, cyclaniliprole, cycloxaprid, dicrotophos, dichlofenthion, cyclobutrifluram, cycloprothrin, dichlorvos, dicloromezotiaz, dicofol, dicyclanil, disulfoton, dinotefuran, dinobuton, cyhalodiamide, cyhalothrin [including gamma-form and lambda-form], cyphenothrin [including (1R)-trans-form], cyfluthrin [including beta-form], diflubenzuron, cyflumetofen, diflovidazin, cyproflanilide, cyhexatin, cypermethrin [including alpha-form, beta-form, theta-form, and zeta-form], dimpropyridaz, dimethyl-2,2,2-trichloro-1-hydroxyethyl phosphonate (DEP), dimethylvinphos, dimethoate, dimefluthrin, jasmone, cis-jasmone, jasmonic acid, methyl jasmonate, silafluofen, cyromazine, Steinernema carpocapsae, Steinernema kushidai, Steinernema glaseri, spidoxamat, spinetoram, spinosad, spirodiclofen, spirotetramat, spiropidion, spiromesifen, sulcofuron-sodium, sulfluramid, sulfoxaflor, sulfotep, diazinon, thiacloprid, thiamethoxam, tioxazafen, thiodicarb, thiocyclam, thiosultap, thionazin, thiofanox, thiometon, tyclopyrazoflor, tetrachlorantraniliprole, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, *Trichoderma asperellum, Trichoderma harzianum*, triflumuron, triflumezopyrim, trimethacarb, tolfenpyrad, naled, nicotine, nicofluprole, nitenpyram, nemadectin, densovirus, novaluron, noviflumuron, *Paecilomyces lilacinus, Barkholderia cepacia, Barkholderia rinojensis, Verticillium* lecanii, hydroprene, Pasteuria nishizawae, Pasteuria *penetrans, Bacillus thuringiensis*, entomotoxins produced by *Bacillus thuringiensis, Bacillus thuringiensis* subsp. Aizawai, *Bacillus thuringiensis* subsp. *Israelensis, Bacillus thuringiensis* subsp. Kurstaki, *Bacillus thuringiensis* subsp. Tenebrionis, *Bacillus popilliae, Bacillus licheniformis*, vamidothion, parathion, parathion-methyl, halfenprox, halofenozide, bioallethrin, bioallethrin S-cyclopentenyl, bioresmethrin, bis-(2-chloro-1-methylethyl)ether (DCIP), bistrifluron, hydramethylnon, bifenazate, bifenthrin, pyflubumide, piperonyl butoxide, pymetrozine, pyraclofos, pyrafluprole, pyridaphenthion, pyridaben, pyridalyl, pyrifluquinazon, pyriprole, pyriproxyfen, pirimicarb, pyrimidifen, pyriminostrobin, pirimiphos-methyl, pyrethrine, famphur, fipronil, fenazaquin, fenamiphos, fenitrothion, fenoxycarb, fenothiocarb, phenothrin [including (1R)-trans-form], fenobucarb, fenthion, phenthoate, fenvalerate, fenpyroximate, fenbutatin oxide, fenpropathrin, fonofos, sulfuryl fluoride, butocarboxim, butoxycarboxim, buprofezin, furathiocarb, prallethrin, fluacrypyrim, fluazaindolizine, fluazuron, fluensulfone, fluopyram, sodium fluoroacetate, fluxametamide, flucycloxuron, flucythrinate, flusulfamide, fluthrin, fluvalinate) [including tau-form], flupyradifurone, flupyrazofos, flupyrimin, flufiprole, flufenerim, flufenoxystrobin, flufenoxuron, fluhexafon, flubendiamide, flupentiofenox, flumethrin, fluralaner, flurimfen, prothiofos, protrifenbute, flonicamid, propaphos, propargite, prohydrojasmon, profenofos, broflanilide, profluthrin, propetamphos, propoxur, flometoquin, bromopropylate, hexythiazox, hexaflumuron, *Paecilomyces tenuipes, Paecilomyces fumosoroceus, Paecilomyces lilacinus*, heptafluthrin, heptenophos, permethrin, benclothiaz, benzpyrimoxan, bensultap, benzoximate, bendiocarb, benfuracarb, *Pochonia chlamydosporia, Beauveria tenella, Beauveria bassiana, Beauveria brongniartii*, phoxim, phosalone, fosthiazate, fosthietan, phosphamidon, phosmet, polynactin complex, formetanate, phorate, machine oil, malathion, milbemectin, mecarbam, mesulfenfos, methomyl, metaldehyde, metaflumizone, methamidophos, metham, methiocarb, methidathion, methyl isothiocyanate, methyl bromide, methoxychlor, methoxyfenozide, methothrin, metofluthrin, methoprene, metolcarb, mevinphos, meperfluthrin, Monacrosporium phymatophagum, Monacrosporium phymatophagum, monocrotophos, momfluorothrin, *Trichoderma harzianum*, litlure-A, litlure-B, aluminium phosphide, zinc phosphide, phosphine, lufenuron, rescalure, resmethrin, lepimectin, rotenone, cytoplasmic polyhedrosis virus, fenbutatin oxide, calcium cyanide, organotins, nicotine-sulfate, (Z)-11-tetradecenyl acetate, (Z)-11-hexadecenal, (Z)-11-hexadecenyl acetate, (Z)-9,12-tetradecadienyl acetate, (Z)-9-tetradecen-1-ol, (Z,E)-9,11-tetradecadienyl acetate, (Z,E)-9,12-tetradecadienyl acetate, 1,1,1-trichloro-2,2-bis(4-chlorophenyl)ethane (DDT), 1,3-dichloropropene, 2,4-dichloro-5-{2-[4-(trifluoromethyl)phenyl]ethoxy}phenyl 2,2,2-trifluoroethyl sulfoxide (IUPAC name; CAS Registry Number: 1472052-11-1), 2,4-dimethyl-5-[6-(trifluoromethylthio)hexyloxy]phenyl-2,2,2-trifluoroethyl sulfoxide (IUPAC name; CAS Registry Number: 1472050-34-2), 2-{2-fluoro-4-methyl-5-[(2,2,2-trifluoroethyl) sulfinyl] phenoxy}-5-(trifluoromethyl)pyridine (IUPAC name; CAS Registry Number: 1448758-62-0), 3-chloro-2-{2-fluoro-4-methyl-5-[(2,2,2-trifluoroethyl) sulfinyl] phenoxy}-5-(trifluoromethyl)pyridine (IUPAC name; CAS Registry Number: 1448761-28-1), 4,6-dinitro-o-cresol (DNOC), 4-fluoro-2-methyl-5-(5,5-dimethylhexyloxy]phenyl 2,2,2-trifluoroethyl sulfoxide (IUPAC name; CAS Registry Number: 1472047-71-4), Bt proteins (Cry1Ab, Cry1Ac, Cry1Fa, Cry2Ab, mCry3A, Cry3Ab, Cry3Bb, Cry34/35Ab1), methyl eugenol, 4-(p-acetoxyphenyl)-2-butanone, (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, 14-methyl-1-octadecene, AKD-1193 (Code Number), BCS-AA10147 (Code Number), CL900167 (Code Number), 0,0-diethyl-O-[4-(dimethylsulfamoyl)phenyl]-phosphorothionate (DSP), O-ethyl-O-4-(nitrophenyl)phenyl phosphonothioate (EPN), RU15525 (Code Number), XMC, Z-13-icosen-10-one, ZXI8901 (Code Number), and F4260 (Code Number).

The following compounds are non-limiting examples of known herbicides, herbicidal active components, and plant growth regulators that can be used as a mixture or in combination.

Herbicide Compounds or Herbicidal Active Components

Ioxynil (including salts, for example, such as lithium salt, sodium salt, and octanoate), aclonifen, acrolein, azafenidin, acifluorfen (including salts, for example, such as sodium salt), azimsulfuron, asulam, acetochlor, atrazine, anisiflupurin, anilofos, amicarbazone, amidosulfuron, amitrole, aminocyclopyrachlor, aminopyralid, amiprofos-methyl, ametryn, Araujia mosaic virus, alachlor, *Alternaria destruens*, alloxydim (including salts, for example, such as sodium salt), ancymidol, isouron, isoxachlortole, isoxaflutole, isoxaben, isodecyl alcohol ethoxylate, isoproturon, ipfencarbazone, imazaquin, imazapic (including salts, for example, such as amine salt), imazapyr (including salts, for example, such as isopropylamine salt), imazamethabenz, imazamethabenz-methyl, imazamox, imazethapyr, imazosulfuron, indaziflam, indanofan, eglinazine-ethyl, esprocarb, ethametsulfuron-methyl, ethalfluralin, ethidimuron, ethoxysulfuron, ethoxyfen, ethoxyfen-ethyl, ethofumesate, etobenzanid, epyrifenacil, endothal-disodium, oxadiazon, oxadiargyl, oxaziclomefone, oxasulfuron, oxyfluorfen, oryzalin, Obuda pepper virus, orthosulfamuron, orbencarb, oleic acid, cafenstrole, caprylic acid, capric acid, carfentrazone-ethyl, karbutilate, carbetamide, quizalofop, quizalofop-ethyl, quizalofop-P-ethyl, quizalofop-P-tefuryl, *Xanthomonas campestris*, quinoclamine, quinclorac, quinmerac, citric acid, cumyluron, clacyfos, glyphosate (including salts, for example, such as sodium salt, potassium salt, amine salt, propylamine salt, isopropylamine salt, ammonium salt, isopropylammonium salt, guanidine salt, monoethanolamine salt, choline salt, BAPMA (N,N-bis-(aminopropyl)methylamine) salt, dimethylamine salt, and trimesium salt), glufosinate (including salts, for example, such as amine salt and sodium salt), glufosinate-P, glufosinate-P-sodium, clethodim, clodinafop, clodinafop-propargyl, clopyralid (including salts, for example, such as monoethanolamine salt), clomazone, chlomethoxyfen, clomeprop, cloransulam-methyl, chloramben, chloridazon, chlorimuron, chlorimuron-ethyl, chlorsulfuron, chlorthal-dimethyl, chlorthiamid, chlorphthalim, chlorflurenol-methyl, chlorpropham, chlorbromuron, chloroxuron, chlorotoluron, ketospiradox (including salts, for example, such as sodium salt, calcium salt, and ammonia salt), *Colletotrichum orbiculare, Colletotrichum gloeosporioides, Colletotrichum truncatum, Chondrostercum purpureum*, saflufenacil, sarmentine, cyanazine, cyanamide, diuron, diethatyl-ethyl, dioxopyritrione, dicamba (including salts, for example, such as amine salt, diethylamine salt, isopropylamine salt, diglycolamine salt, dimethylammonium salt, diolamine salt, isopropylammonium salt, auramine salt, potassium salt, trolamine salt, BAPMA (N,N-bis-(aminopropyl)methylamine) salt, choline salt, sodium salt, and lithium salt; and esters, for example, such as methyl ester), cycloate, cycloxydim, diclosulam, cyclosulfamuron, cyclopyranil, cyclopyrimorate, dichlobenil, diclofop, diclofop-P-methyl, diclofop-methyl, dichlorprop, dichlorprop-P (including salts, for example, such as dimethylammonium salt, potassium salt, sodium salt, and choline salt; and esters, for example, such as butotyl ester, 2-ethylhexyl ester, isoctyl ester, and methyl ester), diquat, diquat dibromide, dithiopyr, siduron, dinitramine, cinidon-ethyl, cinosulfuron, dinoseb (including acetate), dinoterb, cyhalofop, cyhalofop-butyl, cypyrafluone, diphenamid, difenzoquat, diflufenican, diflufenzopyr, simazine, dimesulfazet, dimethachlor, dimethametryn, dimethenamid, dimethenamid-P, simetryn, dimepiperate, dimefuron, *Pseudomonas fluorescens*, cinmethylin, swep, sulcotrione, sulfentrazone, sulfosate, sulfosulfuron, sulfometuron-methyl, sethoxydim, Scelerothinia minor, terbacil, daimuron, thaxtomin A, Tobacco mild green mosaic tobamovirus, Tobacco rattle virus, dalapon, thiazopyr, tiafenacil, thiencarbazone (including, for example, sodium salt, and methyl ester), tiocarbazil, thiobencarb, thidiazimin, thidiazuron, thifensulfuron, thifensulfuron-methyl, desmedipham, desmetryne, tetflupyrolimet, thenylchlor, tebutam, tebuthiuron, tepraloxydim, tefuryltrione, terbuthylazine, terbutryn, terbumeton, tembotrione, topramezone, tralkoxydim, triaziflam, triasulfuron, triafamone, tri-allate, trietazine, triclopyr, triclopyr-butotyl, triclopyr-triethylammonium, tritosulfuron, tripyrasulfone, trifludimoxazin, triflusulfuron-methyl, trifluralin, trifloxysulfuron (including salts, for example, such as sodium salt), tribenuron-methyl, tolpyralate, naptalam (including salts, for example, such as sodium salt), naproanilide, napropamide, napropamide-M, nicosulfuron, lactic acid, neburon, norflurazon, *Burkholderia* rinojensis, vernolate, paraquat, paraquat dichloride, halauxifen, halauxifen-benzyl, halauxifen-methyl, haloxyfop, haloxyfop-P, haloxyfop-etotyl, haloxyfop-P-methyl, halosafen, halosulfuron-methyl, bixlozone, picloram (including salts, for example, such as dichloroammonium salt, and trolamine salt), picolinafen, bicyclopyrone, bispyribac-sodium, pinoxaden, bipyrazone, bifenox, piperophos, pyraclonil, pyrasulfotole, pyrazoxyfen, pyrazosulfuron-ethyl, pyrazolynate, bilanafos, pyraflufen, pyraflufen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, *Phytophthora palmivora*, phenisopham, fenuron, fenoxasulfone, fenoxaprop (including methyl, ethyl, and isopropyl esters), fenoxaprop-P (including methyl, ethyl, and isopropyl esters), fenquinotrione, fenthiaprop-ethyl, fentrazamide, fenpyrazone, phenmedipham, *Phoma chenopodicola, Phoma herbarum, Phoma macrostoma*, butachlor, butafenacil, butamifos, butylate, *Puccinia canaliculata, Puccinia thlaspeos*, butenachlor, butralin, butroxydim, flazasulfuron, flamprop (including methyl, ethyl, and isopropyl esters), flamprop-M (including methyl, ethyl, and isopropyl esters), primisulfuron, primisulfuron-methyl, fluazifop-butyl, fluazifop-P, fluazifop-P-butyl, fluazolate, fluometuron, fluoroglycofen-ethyl, flucarbazone-sodium, fluchloralin, flucetosulfuron, fluthiacet-methyl, flupyrsulfuron-methyl (including salts, for example, such as sodium salt, calcium salt, and ammonia salt), flufenacet, flufenpyr-ethyl, flupropanate (including sodium salt), flupoxame, flumioxazin, flumiclorac-pentyl, flumetsulam, fluridone, flurtamone, fluroxypyr (including ester forms, for example, such as butomethyl ester and meptyl ester, and salts, for example, such as sodium salt, calcium salt, and ammonia salt), flurochloridone, pretilachlor, procarbazone (including salts, for example, such as sodium salt), prodiamine, prosulfuron, prosulfocarb, propaquizafop, propachlor, propazine, propanil, propyzamide, propisochlor, propyrisulfuron, propham, profluazol, prohexadione-calcium, propoxycarbazone, propoxycarbazone-sodium, profoxydim, bromacil, brompyrazon, prometryn, prometon, bromoxynil (including ester forms, for example, such as butyric acid ester, octanoic acid ester, and heptanoic acid ester), bromofenoxim, bromobutide, florasulam, florpyrauxifen, florpyrauxifen-benzyl, hexazinone, pethoxamid, benazolin, benazolin-ethyl, penoxsulam, Pepino mosaic virus, heptamaloxyloglucan, beflubutamid, beflubutamid-M, pebulate, pelargonic acid, bencarbazone, benquitrione, benzfendizone, bensulide, bensulfuron, bensulfuron-methyl, benzobicyclon, benzofenap, bentazone, pentanochlor, pendimethalin, pentoxazone, benfluralin, benfuresate, fosamine, fomesafen, foramsulfuron, forchlorfenuron, mecoprop (including salts, for example, such as sodium salt, potassium salt, isopropylamine salt, triethanolamine salt, dimethylamine salt, diolamine salt, trolamine salt, and choline salt; and esters, for example, such as ethadyl ester, 2-ethylhexyl ester, isoctyl ester, and methyl ester), mecoprop-P-potassium, mesosulfuron (including ester forms, for example, such as methyl ester), mesotrione, metazachlor, metazosulfuron, methabenzthiazuron, metamitron, metamifop, metam (including salts, for example, such as sodium salt), disodium methyl arsonate (DSMA), methiozolin, methyldymuron, metoxuron, metosulam, metsulfuron-methyl, metobromuron, metobenzuron, metolachlor, metribuzin, mepiquat chloride, mefenacet, monosulfuron (including methyl ester, ethyl ester, and isopropyl ester), monolinuron, molinate, iodosulfuron, iodosulfulon-methyl-sodium, iofensulfuron, iofensulfuron-sodium, lactofen, lancotrione, linuron, rimisoxafen, rimsulfuron, lenacil, 2,2,2-trichloroacetic acid (TCA) (including salts, for example, such as sodium salt, calcium salt, and ammonia salt), 2,3,6-trichlorobenzoic acid (2,3,6-TBA), 2,4,5-trichlorophenoxyacetic acid (2,4,5-T), 2,4-dichlorophenoxyacetic acid (2,4-D) (including salts, for example, such as amine salt, diethylamine salt, triethanolamine salt, isopropylamine salt, dimethylammonium salt, diolamine salt, dodecylammonium salt, heptylammonium salt, tetradecylammonium salt, triethylammonium salt, tris(2-hydroxypropyl) ammonium salt, trolamine salt, choline salt, sodium salt, and lithium salt; and esters, for example, such as butotyl ester, 2-butoxypropyl ester, 2-ethylhexyl ester, methyl ester, ethyl ester, butyl ester, isobutyl ester, octyl ester, pentyl ester, propyl ester, isoctyl ester, isopropyl ester, meptyl ester, and tefuryl ester), 2,4-dichlorophenoxybutyric acid (2,4-DB) (including salts, for example, such as amine salt, diethylamine salt, triethanolamine salt, isopropylamine salt, dimethylammonium salt, choline salt, sodium salt, and lithium salt; and esters, for example, such as isoctyl ester), 2-amino-3-chloro-1,4-naphthoquinone (ACN), 2-methyl-4-chlorophenoxyacetic acid (MCPA) (including salts, for example, such as sodium salt, dimethylammonium salt, and choline salt; and esters, for example, such as 2-ethylhexyl ester, isoctyl ester, and ethyl ester), 2-methyl-4-chlorophenoxybutyric acid (MCPB) (including, for example, sodium salt, and ethyl ester), 4-(2,4-dichlorophenoxy)butyric acid (2,4-DB), 4,6-dinitro-O-cresol (DNOC) (including salts, for example, such as amine salt and sodium salt), (5S)-3-(3,5-difluorophenyl)-N-[rel-(3R,5R)-5-(trifluoromethylsulfonylcarbamoyl)tetrahydrofuran-3-yl]-5-vinyl-4H-isoxazole-5-carboxamid) (IUPAC name; CAS Registry Number: 2266183-40-6; WO2018/228986, WO2020/114934), N4-(2,6-difluorophenyl)-6-(1-fluoro-1-methyl-ethyl)-1,3,5-triazine-2,4-diamine) (IUPAC name; CAS Registry Number: 1606999-43-2; WO2014/064094, WO2015/162164), (5S)-3-(3,5-difluorophenyl)-N-[(3R)-5-(methylsulfonylcarbamoyl)-2,3-dihydrofuran-3-yl]-5-vinyl-4H-isoxazole-5-carboxamid) (IUPAC name; CAS Registry Number: 2266190-06-9; WO2018/228986, WO2020/114934), (5R)-3-(3,5-difluorophenyl)-5-methyl-N-[rel-(3R,5R)-5-(methylsulfonylcarbamoyl)tetrahydrofuran-3-yl]-4H-isoxazole-5-carboxamid) (IUPAC name; CAS Registry Number: 2266164-36-5; WO2018/228986, WO2020/114934), (5R)-3-(3,5-difluorophenyl)-N-[(3R)-5-(methoxycarbamoyl)-2,3-dihydrofuran-3-yl]-5-methyl-4H-isoxazole-5-carboxamid) (IUPAC name; CAS Registry Number: 2266170-31-2; WO2018/228986, WO2020/114934), 2-[2-(3,4-dimethoxyphenyl)-6-methyl-3-oxo-pyridazine-4-carbonyl]cyclohexane-1,3-dione) (IUPAC name; CAS Registry Number: 2138855-12-4; WO2017/178582, WO2018/015476), 4-hydroxy-1-methyl-3-[4-(trifluoromethyl)-2-pyridyl]imidazolidin-2-one) (IUPAC name; CAS Registry Number: 1708087-22-2; WO2015/059262, WO2018/015476), 6-(1-fluorocyclopentyl)-N4-(2,3,5,6-tetrafluorophenyl)-1,3,5-triazine-2,4-diamine) (IUPAC name; CAS Registry Number: 1820807-75-7; WO2015/162164), 6-(1-fluoro-1-methyl-ethyl)-N4-(2,3,5,6-tetrafluorophenyl)-1,3,5-triazine-2,4-diamine) (IUPAC name; CAS Registry Number: 1606999-21-6; WO2014/064094, WO2015/162164), (5S)-3-(3-fluoro-5-methyl-phenyl)-N-[rel-(3R,5R)-5-(methoxycarbamoyl)tetrahydrofuran-3-yl]-5-vinyl-4H-isoxazole-5-carboxamid) (IUPAC name; CAS Registry Number: 2266292-43-5; WO2018/228986, WO2020/114934), 6-(1-methylcyclobutyl)-N4-(2,3,5,6-tetrafluorophenyl)-1,3,5-triazine-4,4-diamine) (IUPAC name; CAS Registry Number: 1607001-97-7; WO2014/064094, WO2015/162164), AE-F-150944 (Code Number), F9960 (Code Number), IR-6396 (Code Number), MCPA-thioethyl, NC-656 (Code Number), SYP-298 (Code Number), SYP-300 (Code Number), S-ethyldipropylthiocarbamate (EPTC), S-metolachlor, S-9750 (Code Number), MSMA, HW-02 (Code Number), S-523 (Code Number), and SL-1201 (Code Number).

Plant Growth Regulators

1-Naphthylacetamide, 1-methylcyclopropene, 1,3-diphenylurea, 2,3,5-triiodobenzoic acid, 2-methyl-4-chlorophenoxybutyric acid (MCPB) [including, for example, sodium salt, and ethyl ester], 2-(naphthalene-1-yl)acetamide, 2,6-diisopropylnaphthalene, 3-[(6-chloro-4-phenylquinazoline-2-yl)amino]propane-1-ol, 4-oxo-4-(2-phenylethyl)aminobutyric acid (IUPAC name; CAS Registry Number: 1083-55-2), 4-chlorophenoxyacetic acid (4-CPA), 5-aminolevulinic acid hydrochloride, methyl 5-(trifluoromethyl)benzo[b]thiofen-2-carboxylate, AVG (aminoethoxyvinylglycine), n-decyl alcohol (n-decanol), anisiflupurin, aviglycine, ancymidol, abscisic acid, isoprothiolane, inabenfide, indole acetic acid, indole butyric acid, uniconazole, uniconazole-P, Ecolyst, ethychlozate, ethephon, epocholeone, calcium chloride, choline chloride, oxine-sulfate, opabactin, kinetin, calcium peroxide, carvone, quinabactin, calcium formate, cloxyfonac, cloxyfonac-potassium, cloprop, chlormequat, chlormequat-chloride, chlorpropham, choline, cytokinins, oxidized glutathione, cyanamide, sodium cyanate, cyclanilide, dichlorprop (including salts, for example, such as dimethylammonium salt, potassium salt, sodium salt, and choline salt; and esters, for example, such as butotyl ester, 2-ethylhexyl ester, isoctyl ester, and methyl ester), dichlorprop-P (including salts, for example, such as sodium salt, potassium salt, and dimethylammonium salt; and 2-ethylhexyl ester), diquat, diquat dibromide, dikegulac, gibberellinic acid, gibberellin A4, gibberellin A7, dimethipin, sintofen, jasmone, cis-jasmone, jasmonic acid, methyl jasmonate, streptomycin, calcium polysulfide, daminozide, calcium carbonate, thidiazuron, decan-1-ol, triacontanol, triapenthenol, trinexapac-ethyl, tribufos, paclobutrazol, paraffin, bispyribac-sodium, hymexazol, butralin, fluthiacet-methyl, pyraflufen-ethyl, flumetralin, flurprimidol, flurenol, pronitridine, prohydrojasmon, prohexadione-calcium, heptamaloxyloglucan, 6-benzylaminopurine, pendimethalin, forchlorfenuron, formononetin, maleic hydrazide, mepiquat chloride, mefluidide, lipochitooligosaccharides (for example, lipochitooligosaccharides SP104), and calcium sulfate.

The following are non-limiting examples of known safener compounds that can be used as a mixture or in combination.

Safener Compounds

Isoxadifen, isoxadifen-ethyl, oxabetrinil, octane-1,8-diamine, cloquintocet, cloquintcet-mexyl, dietholate, cyometrinil, dichlormid, dicyclonone, cyprosulfamide, daimuron, 1,8-naphthalic anhydride, fenchlorazole, fenchlorazole-O-ethyl, fenclorim, furilazole, fluxofenim, flurazole, benoxacor, metcamifen, mephenate, mefenpyr, mefenpyr-ethyl, mefenpyr-diethyl, lower alkyl substituted benzoic acid, 2,2-dichloro-N-(1,3-dioxolan-2-ylmethyl)-N-(2-propenyl)acetamide (PPG-1292), 2-dichloromethyl-2-methyl-1,3-dioxane (MG-191), 3-dichloroacetyl-2,2,5-trimethyl-1,3-oxazolidine (R-29148), 4-dichloroacetyl-1-oxa-4-azaspiro[4.5]decane (AD-67), 4-carboxy-3,4-dihydro-2H-1-benzopyran-4-acetic acid (CL-304415, Code Number), MON4660 (Code Number), metcamifen, N1,N2-diallyl-N2-dichloroacetylglycineamide (DKA-24, Code Number), 1-bromo-4-[(chloromethyl)sulfonyl]benzene (CSB), 2-propenyl 1-oxa-4-azaspiro[4,5]decane-4-carbodithioate (MG-838, Code Number), 3-(dichloroacetyl)-2,2-dimethyl-1,3-oxazolidine (R-28725, Code Number), R-29148 (Code Number), and 1-(dichloroacetyl)azepane (TI-35, Code Number).

The following are non-limiting examples of known biopesticides that can be used as a mixture or in combination.

Biopesticides

*Haplothrips brevitubus, Franklinothrips vespiformis, Diglyphus isaea, Encarsia formosa, Amblyseius cucumeris, Pseudaphycus malinus, Amblyseius womersleyi, Aphidius colemani, Eretmocerus eremicus, Aphidoletes aphidimyza, Amblyseius swirskii, Orius strigicollis, Phytoseiulus persimilis, Amblyseius degenerans, Phytoseiulus persimilis, Orius sauteri, Dacnusa sibirica, Amblyseius californicus, Chrysoperla nipponensis*, and *Anicetus beneficus.*

The following are non-limiting examples of known agricultural materials that can be used as a mixture or in combination.

Agricultural Materials

Ethylene, a hypochlorous acid solution (only those produced by electrolysis of hydrochloric acid or an aqueous solution of potassium chloride), baking soda, vinegar, humus, humic acid, fulvic acid, seaweed extracts, polysaccharides, amino acids, microbial materials, functional components derived from animals and plants, microbial metabolites, microbial active materials, soil spreading agents, soil-systemic regulatory material, soil-water retaining materials, and biostimulants.

The following are non-limiting examples of known agricultural fertilizer components that can be used as a mixture or in combination.

Fertilizers include inorganic fertilizers and organic fertilizers. Examples include ammonium chloride, ammonium sulfate, ammonium nitrate, ammonium dihydrogenphosphate, urea ammonium nitrate, urea, nitrolime, potassium nitrate, superphosphate, double superphosphate, potassium dihydrogen phosphate, potassium chloride, potassium sulfate, potassium carbonate, potassium silicate, oil meal, fish meal, rice bran, bat guano, and fermented chicken manure.

The agents of the present invention, including a plant growth regulator and a soil-borne plant disease control agent, are also applicable to plants that have acquired properties such as pest resistance, disease resistance, and herbicide resistance by techniques such as newer breeding techniques (e.g., genetic recombination, genome editing), and artificial crossing.

As described above, the present invention uses viable bacteria of the bacterial strain *Lysinibacillus xylanilyticus* GIC41, or a culture containing the viable bacteria, as an active component. In this way, the present invention can provide a material that can contribute to crop production by increasing profit with its plant growth regulatory effect while reducing loss by controlling disease.

The following describes Examples of the present invention. It is to be noted, however, that the present invention is not limited to the Examples below, and various modifications are possible within the technical idea of the present invention.

Example 1

Separation and Identification of GIC41 Bacterial Strain

A sample of paddy soil collected in Mie prefecture, Japan, was suspended in sterile water, and subjected to a heat treatment at 80° C. for 20 minutes. After being allowed to cool, the suspension was applied to NA medium (dry bouillon 0.3%, agar 1.5%, pH 7.0), and cultured at 30° C. for 24 hours. After culture, colonies appeared on NA medium were harvested and purified to obtain a pure bacterial strain. A molecular phylogenetic analysis of the base sequence of the 16S-rRNA gene identified the GIC41 bacterial strain as the same species as *Lysinibacillus xylanilyticus*, or a species related to *Lysinibacillus xylanilyticus* (FIG. 1).

Example 2

Test on Growth Promoting Effect for Spinach by Irrigation Treatment

Spinach seeds (variety: late-bolting summer sky) were treated at 4° C. for 1 day to break dormancy, and sowed in a cell tray filled with planting soil. The seeds were grown at 23° C. for 7 days with a 12-hour day length. After growth, the seedlings were irrigated with a GIC41 bacterial strain suspension (10 ml per seedling). For comparison, a group of seedlings was irrigated with the same amount of a 10 mM magnesium chloride aqueous solution (control group). The seedlings were then transplanted to planters filled with planting soil (5 seedlings per planter), and grown for 6 weeks in a glasshouse. The aboveground part of the grown plant was dried for 2 days in a hot-air dryer set at 80° C., and the dry weight was measured. The plants were photographed.

The GIC41 bacterial strain suspension was prepared by harvesting cells by centrifugation after 48-hour shake culture in NB medium (dry bouillon 0.3%, pH 7.0) at 30° C., 200 rpm, and suspending the cells in a 10 mM magnesium chloride aqueous solution before centrifugation and harvest. This procedure was repeated twice to prepare a bacterial suspension with an absorbance at 600 nm ($OD_{600}$) of 0.5 (about $1\times10^7$ cfu/mL).

Figure 2:
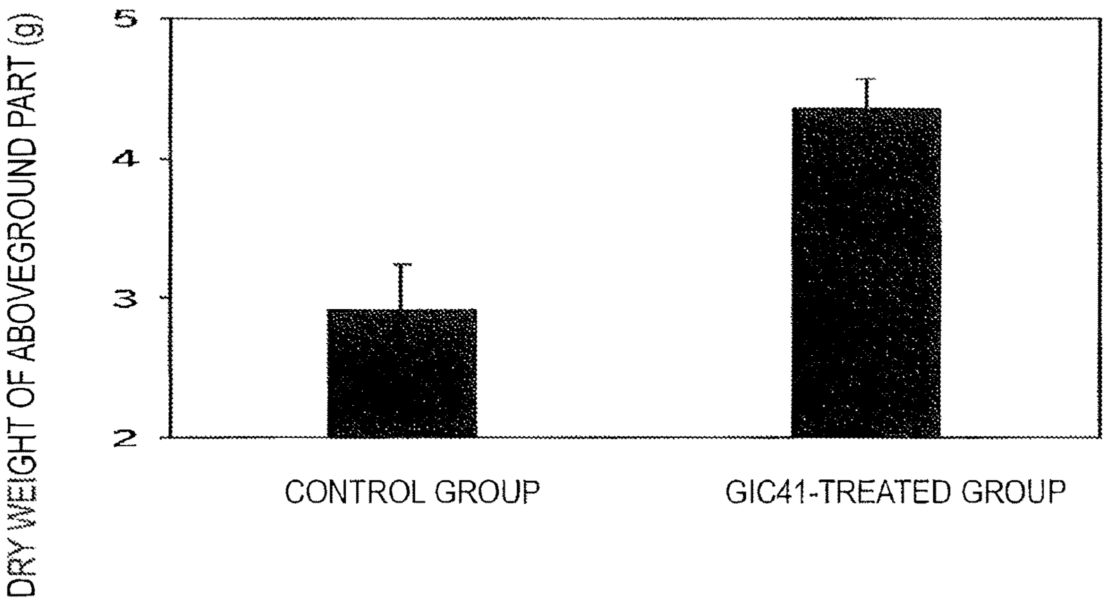
FIG. 2 shows the dry weight of the aboveground part of spinach in Example 2.
Figure 3:
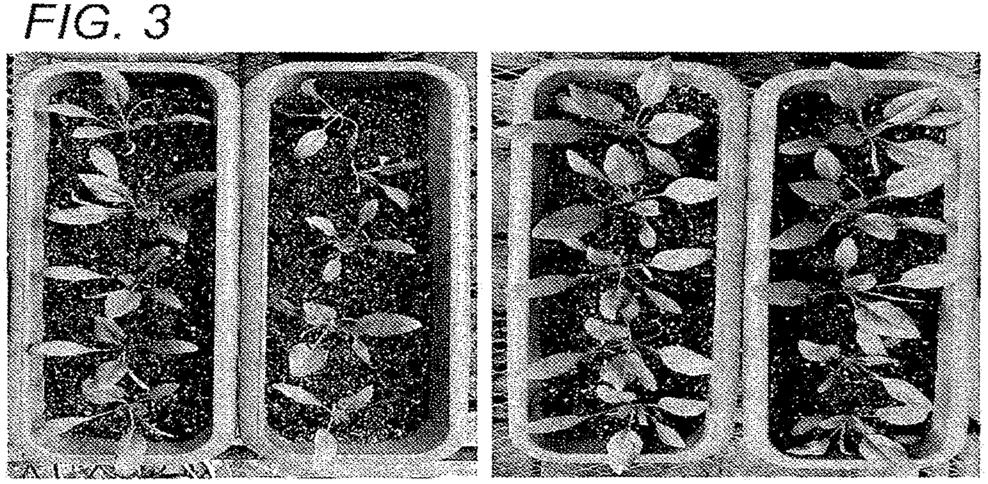
FIG. 3 shows photographs of spinach in Example 2, in which the pictures of the two planters on the left-hand side represent the control group, and the pictures of the two planters on the right-hand side represent a GIC41 bacterial strain group treated by irrigation.

The results are shown in FIGS. 2 and 3 (photographic substitutes for drawings). In contrast to the spinach of the control group that had an aboveground part dry weight of about 2.9 g on average, the GIC41 bacterial strain-treated group had an average dry weight of about 4.4 g in the aboveground part, showing that growth of the aboveground part was greatly promoted. FIG. 2 is a photographic substitute for drawing representing the growth promoting effect of the GIC41 strain.

Example 3

Comparative Test on Growth Promoting Effect for Spinach by Irrigation Treatment and Seed Treatment A suspension of GIC41 strain for irrigation treatment was prepared by harvesting cells by centrifugation after 48-hour shake culture in NB medium at 30° C., 200 rpm, and suspending the cells in a 10 mM magnesium chloride aqueous solution before centrifugation and harvest. This procedure was repeated twice to prepare a bacterial suspension with an absorbance at 600 nm ($OD_{600}$) of 0.5 (about $1\times10^{7}$ cfu/mL). For seed treatment, the GIC41 bacterial strain was shake cultured in modified Schaeffer medium (nutrient broth 1.6%, potassium chloride 0.2%, magnesium sulfate-7 hydrate 0.05%, 1 mM calcium nitrate, 0.01 mM manganese chloride, 0.001 mM ferrous sulfate) at 30° C., 200 rpm for 72 hours. The culture was centrifuged (10,000 rpm, 10 minutes), and the harvested cells were suspended in cold sterilized water before centrifugation and harvest. This procedure was repeated 10 times. Lysozyme (50 μg/mL) was added to the suspension, and a reaction was allowed for 10 minutes under ice cooling. After removing feeder cells, the culture was sonicated 6 times, 15 seconds for each run, in ice water. To the resulting suspension of endospores, an equal amount of 2% carboxymethyl cellulose was added.

Spinach seeds (variety: late-bolting summer sky) were treated at a low temperature of 4° C. for 1 day to break dormancy, and sowed in planting soil in a 9 cm pot. The soil was irrigated with 5 ml of a GIC41 bacterial strain suspension as a GIC41 bacterial strain irrigation treatment group. For comparison, an equal amount of a 10 mM magnesium chloride aqueous solution was added for irrigation treatment (control group). Separately, spinach seeds, brought out of dormancy, were coated with carboxymethyl cellulose mixed with GIC41 bacterial strain, and the seeds were sowed in planting soil in a 9 cm pot as a GIC41 bacterial strain seed treatment group. In the control group, the seeds were coated with carboxymethyl cellulose without GIC41 bacterial strain.

The pots were kept in a glasshouse for 4 weeks, and the aboveground part of spinach was picked for the measurement of a fresh weight.

Figure 4:
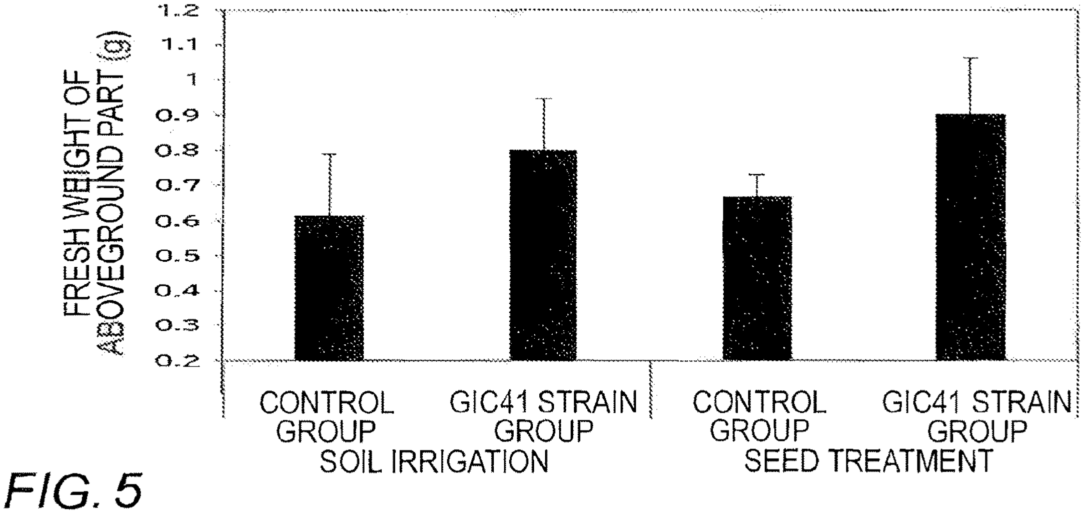
FIG. 4 shows the fresh weight of the aboveground part of spinach in Example 3.

The test results are shown in FIG. 4. In the control group, the aboveground part of spinach was, on average, about 0.61 g in fresh weight after the irrigation treatment, and about 0.67 g in fresh weight after the seed treatment. In contrast, the average fresh weight of the aboveground part was about 0.80 g in the irrigation treatment group, and about 0.90 g in the seed treatment group after treatment with the GIC41 bacterial strain, showing that growth of the aboveground part was greatly promoted in both the irrigation treatment and the seed treatment.

Example 4

Test on Growth Promoting Effect for Sugar Beet by Irrigation

Treatment A sugar beet (variety: Papirika) was grown to the four leaf stage in a sugar-beet paper pot (a set of 1,400 (20 rows×70 columns) specially-made paper cylinders bound together, each measuring 19 mm in diameter and 130 mm in length with an open top and bottom) filled with planting soil (Yosaku®, manufactured by JCAM AGRI Co., Ltd.). The sugar beet was then irrigated at the base of the plant with 0.71 ml of a GIC41 bacterial strain suspension per stock of sugar beet. For comparison, the same amount of water was used for irrigation treatment (control group). The suspension of GIC41 bacterial strain was prepared by harvesting cells by centrifugation (4500×g, 15 minutes) after 48-hour shake culture in nutrient broth medium (meat extract 0.5%, tripeptone 1.0%, sodium chloride 0.5%, pH 7.2) at 30° C., 200 rpm, and suspending the cells in a 10 mM magnesium chloride aqueous solution. This procedure was repeated 3 times, and the absorbance at 600 nm ($OD_{600}$) was adjusted to 0.5 (about $1\times10^{7}$ cfu/mL) with a 10 mM magnesium chloride aqueous solution.

On the next day of irrigation treatment, the plant was transplanted to a plastic cup (T-600, Tomei Chemical Industrial Co., Ltd.; 13 cm in height, 9 cm in diameter at the top, 6 cm in diameter at the bottom) filled with a 4:1 mix of red ball earth and black earth.

After 28 days from transplantation, the fresh weight of the aboveground part of sugar beet was determined by calculations. Separately, the dry weight of the taproot portion was determined by measuring the weight of the taproot portion after keeping this portion of the plant in a 120° C. drier for 3 days. The weight ratio to control group was calculated using the following formula.

$$\text{Weight ratio to control group} = (\text{weight in treatment group}/\text{weight in control group})\times 100$$

The test results are presented in Table 1 below. In the control group, the aboveground part was 5.81 g/stock in fresh weight, and the taproot portion had a dry weight of 0.42 g/stock. In contrast, the GIC41-treated group had a fresh weight of 6.27 g/stock in the aboveground part, and a dry weight of 0.50 g/stock in the taproot portion, higher than the fresh weight of the aboveground part and the dry weight of the taproot portion measured in the control. As demonstrated above, the GIC41 bacterial strain showed a growth promoting effect on sugar beet.

TABLE 1

| Bacterial strain | Fresh weight of aboveground part (g/stock) | Weight ratio of fresh weight of aboveground part against control group (%) | Dry weight of taproot portion (g/stock) | Weight ratio of dry weight of taproot portion against control group (%) |
|---|---|---|---|---|
| GIC41 | 6.27 | 108 | 0.50 | 119 |
| Control group | 5.81 | — | 0.42 | — |

Example 5

Test on Growth Promoting Effect for Potato by Spraying to Stems and Leaves

A potato (variety: Dejima) was grown to the five compound leaf stage in a plastic cup (T-600, Tomei Chemical Industrial Co., Ltd.; 13 cm in height, 9 cm in diameter at the top, 6 cm in diameter at the bottom) filled with a 4:1 mix of red ball earth and black earth. After growth, a GIC41 bacterial strain suspension was sprayed to stems and leaves from above the pot with a hand sprayer in an amount equivalent of 100 L/10a, a total of 3 times at one-week intervals. For comparison, the same amount of water was sprayed to stems and leaves (control group). The GIC41 bacterial strain suspension was prepared by harvesting cells by centrifugation (4500×g, 15 minutes) after 48-hour shake culture in nutrient broth medium (meat extract 0.5%, tripeptone 1.0%, sodium chloride 0.5%, pH 7.2) at 30° C., 200 rpm, and suspending the cells in a 10 mM magnesium chloride aqueous solution. This procedure was repeated 3 times, and the absorbance at 600 nm ($OD_{600}$) was adjusted to 0.5 (about $1\times10^7$ cfu/mL) with a 10 mM magnesium chloride aqueous solution.

After one week from the last application, the fresh weight of the aboveground part of potato was measured. Separately, the dry weight of the underground part was measured by keeping this part of the plant in a 120° C. drier for 3 days. The weight ratio to control group was calculated using the formula of Example 4.

The test results are presented in Table 2 below. In the control group, the aboveground part was 8.39 g/stock in fresh weight, and the underground part had a dry weight of 0.83 g/stock. In contrast, the GIC41-treated group had a fresh weight of 8.39 g/stock in the aboveground part, and a dry weight of 1.00 g/stock in the underground part. The fresh weight of the aboveground part was the same in the control group and the GIC41-treated group. However, the dry weight of the underground part was higher in the GIC41-treated group than in the control group. As demonstrated above, the GIC41 bacterial strain showed a growth promoting effect on potato.

TABLE 2

| Bacterial strain | Fresh weight of aboveground part (g/stock) | Weight ratio of fresh weight of aboveground part against control group (%) | Dry weight of underground part (g/stock) | Weight ratio of dry weight of underground part against control group (%) |
|---|---|---|---|---|
| GIC41 | 8.39 | 100 | 1.00 | 120 |
| Control group | 8.39 | — | 0.83 | — |

Example 6

Test on Damping-Off Control Effect for Spinach

Three seeds of spinach (variety: late-bolting summer sky), brought out of dormancy, were sowed in planting soil in a 9 cm pot, and the seeds were grown at 23° C. with a 12-hour day length. After 5 days, the plant was irrigated with 5 ml of a GIC41 bacterial strain suspension, together with a damping-off pathogen (*Pythium aphanidermatum*). For comparison, only the pathogen was used for irrigation (control group). The spinach was grown at 23° C. for 16 days with a 12-hour day length. After growth, the extent of damping-off the spinach was investigated according to the following criteria, and in an incidence of disease and control efficacy were calculated. The plants were photographed.

The suspension of GIC41 strain was prepared by harvesting cells by centrifugation after 48-hour shake culture in NB medium (dry bouillon 0.3%, pH 7.0) at 30° C., 200 rpm, and suspending the cells in a 10 mM magnesium chloride aqueous solution before centrifugation and harvest. This procedure was repeated twice to prepare a bacterial suspension with an absorbance at 600 nm ($OD_{600}$) of 0.5 (about $1\times10^7$ cfu/mL). The damping-off pathogen (*Pythium aphanidermatum*) was inoculated to corn meal agar medium (corn meal 2%, peptone 2%, glucose 2%, agar 1.5%), and cultured at 25° C. for 2 days. After culture, a pathogen-containing disc was taken out from around the periphery of a colony, and put in pond water that had been sterilized under high pressure (water collected from a pond was diluted with twice the amount of distilled water as pond water, and sterilized under high pressure). After culture at 25° C. for 1 day, zoospores released into water were collected. A suspension of zoospores was diluted with sterile water, and adjusted to 104 zoospores/ml with a counting chamber.

Disease Index

- 0: No symptoms of disease
- 1: Slight inhibition of growth
- 2: Moderate inhibition of growth, or symptoms of chlorosis
- 3: Severe inhibition of growth, or wilt
- 4: Severe wilt or withering Incidence of Disease and Control Efficacy $$\text{Incidence of disease} = \sum(\text{disease index} \times \text{number of seedlings with corresponding index})/(\text{number of seedlings examined} \times 4) \times 100$$

$$\text{Control efficacy} = 100 - (\text{incidence of disease in treated group}/\text{incidence of disease in control group of inoculation}) \times 100$$

Figure 5:
FIG. 5 shows an incidence of damping-off in spinach of Example 5.

The test results are presented in Table 3 and FIG. 5 (photographic substitute for drawing).

TABLE 3

| | Incidence of disease | Control efficacy |
|---|---|---|
| Control group | 61.1 | — |
| GIC41 bacterial strain group | 19.4 | 68.2 |

The present invention can be summarized as follows.

An objective of the present invention is to provide a material that can contribute to crop production by increasing profit with its plant growth regulatory effect while reducing loss by controlling disease at the actual site of crop production.

In the present invention, viable bacteria of a novel bacterial strain of genus *Lysinibacillus*, unknown in the past, or a culture containing the viable bacteria, are used as an active component. In this way, a plant growth regulator that promotes crop growth and increases yield, and a control agent that controls crop disease can be provided at the same time.

Reference to Deposited Biological Material

The accession number of a microorganism that has been deposited in relation to the present invention is as follows.

(1) *Lysinibacillus xylanilyticus* GIC41 bacterial strain (NITE BP-03464).

What is claimed is:

1. A strain suspension comprising a viable bacterial strain of a *Lysinibacillus xylanilyticus* GIC41 bacterial strain (NITE BP-03464), and/or a culture comprising the viable bacterial strain as an active component and comprising a cell concentration in the range of $1\times10^5$ cfu/mL to $1\times10^{11}$ cfu/mL.

2. The strain suspension according to claim 1, wherein the cell concentration is in the range of $1\times10^6$ to $1\times10^{10}$ cfu/mL.

3. A method for adjusting concentration of a cell composition for application to seeds or a crop comprising:

diluting the cell composition with water to a cell concentration ranging from of $1\times10^5$ cfu/mL to $1\times10^{11}$ cfu/mL.

4. The method according to claim 3, wherein the cell concentration is diluted to a cell concentration ranging from $1\times10^6$ to $1\times10^{10}$ cfu/mL.

5. A method for regulating plant growth, and/or for controlling a plant disease comprising plant damping off, comprising:

contacting a suspension or culture comprising viable bacteria of a *Lysinibacillus xylanilyticus* GIC41 bacterial strain (NITE BP-03464) at a cell concentration of $1\times10^5$ cfu/mL to $1\times10^{11}$ cfu/mL to a plant or plants and/or to the soil.

6. The method according to claim 5, wherein the plant or plants is a plant seed.

7. The method according to claim 5, wherein the plants are Amaranthaceae plant(s) or Solanaceae plant(s).

8. The method according to claim 5, wherein the viable bacteria or the culture containing the viable bacteria are contacted to soil by irrigation or by mixing into the soil.

9. The method according to claim 5, wherein the contacting of the viable bacteria, or of the culture containing the viable bacteria, is to a rhizosphere.

10. The method of claim 5 that is a method for regulating plant growth comprising:

contacting a suspension comprising viable bacteria of the *Lysinibacillus xylanilyticus* GIC41 bacterial strain (NITE BP-03464), or contacting a culture containing the viable bacteria that has a cell concentration ranging from $1\times10^5$ cfu/mL to $1\times10^{11}$ cfu/mL, to a plant or plants and/or soil via irrigation or via mixing into the soil.

11. The method of claim 5 that is a method for controlling a plant damping-off disease comprising:

contacting a suspension comprising viable bacteria of the *Lysinibacillus xylanilyticus* GIC41 bacterial strain (NITE BP-03464), or contacting a culture containing the viable bacteria and cell concentration is $1\times10^5$ cfu/mL to $1\times10^{11}$ cfu/mL, to a plant or plants and/or to the soil via irrigation or via mixing into the soil.

* * * * *